US006585818B2

(12) United States Patent
Thakkar et al.

(10) Patent No.: US 6,585,818 B2
(45) Date of Patent: Jul. 1, 2003

(54) PIGMENT INK FORMULATION

(75) Inventors: Sharad Ramanlal Thakkar, Lexington, KY (US); Jing X. Sun, Lexington, KY (US)

(73) Assignee: Lexmark International, Inc., Lexington, KY (US)

( * ) Notice: Subject to any disclaimer, the term of this patent is extended or adjusted under 35 U.S.C. 154(b) by 74 days.

(21) Appl. No.: 09/923,069

(22) Filed: Aug. 6, 2001

(65) Prior Publication Data

US 2003/0101900 A1 Jun. 5, 2003

Related U.S. Application Data

(63) Continuation-in-part of application No. 09/916,571, filed on Jul. 27, 2001, now Pat. No. 6,402,825.

(51) Int. Cl.$^7$ .............................................. C09D 11/02
(52) U.S. Cl. ................ 106/31.6; 106/31.86; 106/31.75; 106/31.9
(58) Field of Search .................. 106/31.6, 31.86, 106/31.75, 31.9

(56) References Cited

U.S. PATENT DOCUMENTS 6,143,807 A * 11/2000 Lin et al. .................... 523/161
6,153,001 A * 11/2000 Suzuki et al. ............. 106/31.65
6,328,393 B1 * 12/2001 Lin et al. ........................ 347/1
6,375,728 B2 * 4/2002 Yamashita et al. .......... 106/31.6
6,402,825 B1 * 6/2002 Sun ............................. 106/473
6,440,203 B2 * 8/2002 Kato ........................... 106/31.6

* cited by examiner

*Primary Examiner*—Mark L. Bell
*Assistant Examiner*—Veronica F. Faison
(74) *Attorney, Agent, or Firm*—David LaRose; Jacqueline M. Daspit

(57) ABSTRACT

The invention provides an improved ink formulation and method therefore. The formulation includes from about 50 to about 85 percent by weight water, humectant and an organic solvent and a chemically modified carbon black pigment, wherein the chemically modified carbon black pigment contains steric inducing groups on a surface of the carbon black which groups are derived from a steric inducing compound which compound is substantially soluble in the humectant and is reactive with an organic acid halide. The ink jet printer ink formulation containing the chemically modified carbon black has an idle time of greater than about 15 seconds in an ink jet printhead. Improved idle time is important because it reduces nozzle plugging between nozzle firings.

16 Claims, No Drawings

PIGMENT INK FORMULATION

This application is a continuation-in-part of application Ser. No. 09/916,571, filed Jul. 27, 2001, now U.S. Pat. No. 6,402,825, issued Jun. 11, 2002.

FIELD OF THE INVENTION

The invention relates to improved ink formulations and methods for making ink formulations for ink jet printers.

BACKGROUND OF THE INVENTION

Ink jet printing methods use printheads having orifices which eject ink droplets onto a print medium. For higher quality, higher resolution printing applications, the orifices of the printheads have been increased in number and their diameter significantly reduced in size. As the size of the nozzles decrease improved print quality is obtained by use of different ink formulations. Some ink formulations contain only dyes while other formulations contain only pigments or mixtures of pigments and dyes. Pigments have become increasingly useful in ink formulations, particularly black ink formulations to improve the image quality including optical density of the printed image. However, while pigmented ink formulations have some advantages over dye-based ink formulations, pigment-based formulations are often less stable over time than dye-based formulations resulting in operating problems, particularly with higher quality, higher speed ink jet printers which demand significantly better print performance. Accordingly, improved pigment ink formulations and methods for making the formulations are needed to meet the demands of ever improving ink jet printer technology.

SUMMARY OF THE INVENTION

With regard to the above and other objects and advantages thereof, the invention provides ink jet printer ink formulation and method for making the ink formulation. The formulation includes from about 50 to about 85 percent by weight water, humectant, an organic solvent and a chemically modified carbon black pigment, wherein the chemically modified carbon black pigment contains steric inducing groups on a surface of the carbon black which groups are derived from a steric inducing compound, the compound being substantially soluble in the humectant and the compound being reactive with an organic acid halide. The ink jet printer ink formulation containing the chemically modified carbon black has an idle time of greater than about 15 seconds in an ink jet printhead.

In another aspect the invention provides a method for making an ink formulation for an ink jet printer. The method includes mixing from about 1 to about 10 percent by weight of a chemically modified carbon black pigment containing steric inducing groups on a surface of the carbon black with from about 50 to about 85 percent by weight water, humectant and an organic solvent to provide an ink formulation having improved idle time. The steric inducing groups on the carbon black surface are derived from a steric inducing compound, the compound being substantially soluble in the humectant and the compound being reactive with an organic acid halide. The chemically modified carbon black pigment used in the ink formulation has an acid number ranging from about 0.1 to about 0.7.

An important advantage of the invention is the significant increase in idle time exhibited by ink formulations made according to the invention. Without desiring to be bound by theoretical considerations, it is believed that as water evaporates from the ink adjacent the nozzles of a printhead, the properties of the ink composition in the printhead change. Ink formulations used in ink jet printers are a mixture of water, self-dispersing pigment and organic components such as humectants, binders, penetrants, organic solvent and the like. As water evaporates from the ink, the percentage of organic components in the ink formulation increases so that the ink becomes less hydrophilic. As the ink becomes less hydrophilic, the self-dispersing pigment which is strongly hydrophilic is pulled back into the bulk aqueous phase. Idle time is used to measure the short term reliability of the ink. "Idle time" means the time between nozzle firings just before the printhead produces delayed or misdirected ink droplets. Historically, self-dispersing carbon blacks exhibit poor idle times in ink jet printers. The invention greatly improves the idle time of the ink formulation by modifying the surface of the pigment particles so that the particles remain substantially dispersed in the organic components as well as the aqueous components of the ink formulation.

DETAILED DESCRIPTION OF THE PREFERRED EMBODIMENTS

Ink compositions of the invention are generally referred to as "aqueous ink formulations" because a major component of the ink formulation is water, preferably dionized water. Water is preferably present in the ink formulation in an amount ranging from about 50 to about 85 percent by weight based on the total weight of the ink formulation. All of the other components in the ink formulation are present in an amount of less than about 50 percent by weight, hence the majority of the ink formulation is water. The ink formulation, however, preferably contains organic components which are soluble or dispersible in water. These organic components include binders, humectants, penetrants, and other components which enhance the print quality and durability of images printed with the ink formulation.

An important component of the ink formulation is a chemically modified carbon black pigment. The carbon black pigment modified according to the invention is preferably a self-dispersing carbon black pigment. Methods for making self-dispersing carbon black are well known and include reacting carbon black with sodium hypochlorite in an aqueous medium. The proportion by weight of sodium hypochlorite to carbon black is preferably in a range of from about 0.4 to about 5.25 parts hypochlorite per part carbon black by weight. U.S. Pat. No. 3,347,632 to Parker describes a preferred method for making self-dispersing carbon black and the disclosure of the '632 patent is incorporated by reference as if fully set forth herein. A particularly preferred carbon black for making a self-dispersing carbon black is a neutral carbon black available from Cabot Corporation of Billerica, Mass. under the trade name MONARCH 880.

As a result of the reaction between carbon black and sodium hypochlorite, the surface of the carbon black contains carboxyl, hydroxyl and/or carbonyl groups. The carboxyl groups on the surface of the carbon black provide sites for reaction with steric inducing compounds to provide a chemically modified carbon black pigment which exhibits improved idle time in ink formulations containing the carbon black. A process for reacting a self-dispersing carbon black with a compound selected to provide steric inducing groups on the surface of the carbon black is described in more detail below.

Steric inducing groups are attached to the surface of an oxidized carbon black by first reacting a self-dispersing carbon black with an amount of thionyl halide such as thionyl chloride to provide organic acid halide groups on the surface of the carbon black. The acid halide groups are then reacted with a compound which is soluble in the humectant described below and which is reactive with the organic acid halide group on the surface of the carbon black. The compound preferably contains only one terminal group reactive with the acid halide. Such reactive terminal groups include hydroxyl groups, amino groups, thiol groups, and the like.

A preferred class of steric inducing compounds containing one reactive terminal group include monoalkoxy-terminated polyalkylene glycol compounds having an alkylene group containing from 2 to 6 carbon atoms and an alkyl group containing from 1 to 6 carbon atoms. Representative monoalkoxy-terminated polyalkylene glycol compounds include, but are not limited to triethylene glycol monomethyl ether, diethylene glycol monomethyl ether, triethyleneglycol monoethyl ether, diethylene glycol monoethyl ether, triethylene glycol monopropyl ether, diethylene glycol monopropyl ether, triethylene glycol monobutyl ether, diethylene glycol monobutyl ether and the like and mixtures thereof. Other mono-terminated glycol reactants may be used to modify self-dispersible carbon black by lowering the acid number of the carbon black without adversely affecting the water dispersibility thereof. Such glycol reactants have weight average molecular weights ranging from about 100 to about 1000 and include, but not limited to, methoxypolyethylene glycol and poly(ethylene glycol) tetrahydrofurfuryl ether.

Mono-amine terminated compounds may also be used provided the compounds are soluble in the humectant and reactive with the acid halide groups on the surface of the carbon black. Such compounds include, but are not limited to, alkoxy-terminated Jaffamine polyalkylene glycols having a weight average molecular weight ranging from about 500 to about 2500, methoxy-terminated Jeffamine polyethylene glycol, methoxy-terminated Jeffamine polypropylene glycol and methoxy-terminated Jeffamine polyethylene glycol/polypropylene glycol copolymer. The Jeffamine compounds contain primary amino groups attached to the terminus of a polyether backbone also referred to as "polyether amines." The polyether backbone is based either on propylene oxide (PO), ethylene oxide (EO), or mixed EO/PO. Such amine-terminated compounds may be primary amines or secondary amines.

Other compounds reactive with the organic acid halide groups on the carbon black and soluble in the humectant include, but are not limited to, 2-hydroxyethylpyrrolidone, 2-hydroxyethylmorpholine and 2-hydroxyethyloxazolidone and the like.

By reacting a portion of the carboxyl groups on the surface of the carbon black with the steric inducing reactant, the resulting modified carbon black exhibits increased hydrophobic properties sufficient to increase the dissolution or suspension of carbon black in the organic components of the ink formulation. The modified carbon black is preferably present in the ink formulation in an amount ranging from about 1 to about 10 percent by weight carbon black solids based on the total weight of ink formulation.

While it is preferred to use self-dispersing carbon black and modified self-dispersing carbon black, use of non-self-dispersing carbon black in combination with the modified self-dispersing carbon black in the ink formulation has been found to provide additional operational benefits. Accordingly, a preferred ink formulation of the invention also contains a non-self-dispersing carbon black component. The dispersants for the non-self-dispersing carbon black are preferably graft copolymers comprising a hydrophilic polymeric segment, a hydrophobic polymeric segment incorporating a hydrolytically-stable siloxyl substituent, and a stabilizing segment, such as a reactive surfactant macromer, a protective colloid macromer, or a non-siloxyl hydrophobic monomer having a number average molecular weight of from about 1,500 to about 20,000. Non-self-dispersed carbon blacks are described for example in U.S. Pat. No. 5,589,522 to Beach et al. and U.S. Pat. No. 5,656,071 to Kappele et al., the disclosures of which are incorporated herein by reference as if fully set forth and contain from about 1 to about 10 percent by weight graft copolymer, from about 1 to about 10 percent by weight carbon black and from about 75 to about 98 percent by weight deionized water.

The other components of the ink formulation according to the invention may be selected from a binder, a humectant, a penetrant and an organic solvent. The binder is preferably a resin emulsion containing up to about 25 percent by weight resin solids in an aqueous medium. The resin is preferably a polymer derived from butyl and methyl methacrylate and methacrylic acid. A preferred binder solution is available from Rohm and Haas of Philadelphia, Pa. under the trade name ACRYJET 3666. The binder solution is preferably present in the ink formulation in an amount ranging from about 1 to about 10 percent by weight to provide from about 0.25 to about 2.5 percent by weight resin solids based on the total weight of the ink formulation.

A humectant is preferably used in the ink formulation to modify the penetrant and to reduce the evaporation rate of water from the ink. The humectant used in the ink formulation may be selected from alkylene glycols, amides, ethers, carboxylic acids, esters, alcohols, organosulfides, organosulfoxides, sulfones, amino alcohols and ketones. A preferred humectant is a straight chain alkane diol having from 3 to 10 carbon atoms. A particularly preferred humectant is a 1,2-alkyl diol having from 4 to 8 carbon atoms, specifically 1,2-hexanediol or 1,2-pentanediol. The amount of humectant in the ink formulation preferably ranges from about 0.1 to about 2 percent by weight based on the total weight of the ink formulation.

A penetrant is preferably present in the ink formulation to reduce bleeding or otherwise to improve the overall appearance of the printed images. The penetrant is preferably a glycol ether component which may be selected from the group consisting of propylene glycol mono-n-butyl ether, diethylene glycol mono-n-butyl ether, dipropylene glycol mono-n-butyl ether, triethylene glycol mono-n-butyl ether, propylene glycol monomethyl ether, dipropylene glycol monomethyl ether, diethylene glycol mono-t-butyl ether, diethylene glycol monomethyl ether, triethylene glycol monomethyl ether, diethyelene glycol mono-n-hexyl ether. The penetrant is preferably present in the ink formulation in an amount ranging from about 0.1 to about 2 percent by weight based on the total weight of the ink formulation.

The ink formulation of the invention also preferably contains an organic solvent component. The organic solvent preferably includes water-soluble glycols such as ethylene glycol, diethylene glycol, triethylene glycol, propylene glycol, dipropylene glycol, tripropylene glycol, polyethylene glycol, 1,3-propylene glycol, isopropylene glycol, isobutylene glycol, 1,4-butanediol, 1,3-butanediol, 1,5-pentanediol, 1,6-hexanediol, glycerin, mesoerythritol and pentaerythritol. A particularly preferred glycol solvent component is a polyethylene glycol having a weight average molecular weight of not more than about 800. The ink formulation preferably contains from about 2 to about 10 percent by weight of the glycol solvent component.

Optional components may also be included in the ink formulation. Such components include but are not limited to surfactants, biocides, viscosity modifiers, pH adjusters, buffers, antioxidants, conductivity modifiers and the like.

The following examples are given for illustrative purposes and are not meant in any way to limit the invention.

EXAMPLE 1

Carbon black was modified by mixing 40 grams of self-dispersing carbon black having 0.95 milliequivalents of COOH per gram of carbon black on the surface thereof with 30 grams of thionyl chloride and 100 mL of dry methylene chloride in a three neck flask equipped with a condenser, stirrer and nitrogen purge line. The mixture was stirred and heated to reflux for 7 hours, then cooled to a temperature ranging from about 0° to about 5° C. The resulting carbon black product was filtered under vacuum, washed with dry methylene chloride and stored in a sealed flask.

Methoxy polyethylene glycol (12 grams) having a weight average molecular weight of about 350 was added to a second three neck flask. Dry methylene chloride (100 mL) and 3.6 grams of triethylamine was added to the glycol in the flask and the mixture was cooled to 5° C. in an ice bath. The carbon black product from the first reaction was added slowly to the mixture in the second flask under a nitrogen while stirring the mixture and maintaining the temperature at 5° C. When all of the carbon black product had been added, the mixture was stirred overnight at 5° C. The mixture was then oven dried at a temperature ranging from about 60° to about 80° C. for an hour and the dried product was washed with 500 mL of deionized water. The final product was redissolved in potassium hydroxide to obtain a pH of 7.5. Once the pH of 7.5 was obtained, the mixture was stirred in a high speed mixer such as a high speed mixer from Tekmar Dohrmann of Mason, Ohio under the trade name TISSUMIZER for an hour. The particle size of the product was 148 nm. Ultrafiltration was used to further purify the product. The product was titrated and contained 0.115 milliequivalents of COOH/gram of carbon black.

EXAMPLE 2

Carbon black was modified by mixing 40 grams of self-dispersing carbon black having 0.95 milliequivalents of COOH per gram of carbon black on the surface thereof with 10 mole equivalents of thionyl chloride and 150 mL of toluene in a three neck flask equipped with a condenser, stirrer and nitrogen purge line. The mixture was stirred and heated to 50° C. and reacted for 5 hours under a nitrogen atmosphere. The resulting carbon black product was vacuum distilled under 100 mm Hg vacuum at 50° C. to remove the solvent and unreacted thionyl chloride. The carbon product have surface acid chloride groups was cooled to a temperature ranging from about 0° to about 5° C. in an ice bath.

Cold methylene chloride (100 mL) was added to the flask, then 24 milliequivalents (24 grams) of Jeffamine STJ506 (MW 1000) from Huntsman Corporation of Salt Lake City, Utah and 3.3 grams of triethylamine in 20 mL of methylene chloride was added dropwise to the flask. The reaction mixture was stirred overnight at room temperature. The flask containing the reaction product was distilled under vacuum to remove the solvent, then washed with water to remove the triethylaminehydrochloric acid salt. The final product was redispersed in 20% KOH to obtain a pH of 8.0.

EXAMPLE 3

In the following Table 1, ink formulations were prepared with self-dispersing carbon black and with self-dispersing carbon black chemically modified to contain steric inducing groups derived from triethylene glycol monomethyl ether. Samples 1, 2 and 5 in the table contained self-dispersing carbon black in the amount indicated and carbon black dispersed in a terpolymer made according to U.S. Pat. No. 5,714,538 to Beach et al. All of the other components of the formulations are substantially the same, with the exception that samples 2 and 4 have an increased amount of ACRYJET 3666 binder and a reduced amount of deionized water.

Each of samples 5, 6 and 7 were use in three ink cartridges and images were printed with the cartridges to determine idle time. Longer idle times are desirable from a printer operation point of view. Idle time for an ink formulation was determined by first printing reference droplets for all nozzles from an ink cartridge at time zero on a print media. The cartridge was then allowed to idle for specific intermittent periods of time before again firing the same nozzles to print test drops in vicinity of the reference droplets. The idle time was increased incrementally between nozzle firings. The position of the test drops on paper were compared with the reference droplets. The period of time between nozzle firings at which the test drops are delayed or misdirected with respect to the reference droplets is noted and specified as the idle time.

TABLE 1

| Component | Sample 1 | Sample 2 | Sample 3 | Sample 4 | Sample 5 | Sample 6 | Sample 7 |
|---|---|---|---|---|---|---|---|
| SDCB[1] | 2.5 | 2.5 | — | — | 2.5 | — | — |
| ESDCB[2] | — | — | 2.5 | 2.5 | — | 2.5 | 2.5 |
| Dispersed Carbon Black[3] (20 wt. % solids in terpolymer) | 3 | 3 | 3 | 3 | — | — | — |
| Dispersed Carbon Black[3] (16.67 wt. % solids in terpolymer) | — | — | — | — | 3 | 3 | 3 |
| 2-pyrrolidone | 7.5 | 7.5 | 7.5 | 7.5 | 7.5 | 7.5 | 7.5 |
| 1,2-hexanediol | 1.2 | 1.2 | 1.2 | 1.2 | 1.2 | 1.2 | 1.2 |
| Hexyl carbitol | 0.4 | 0.4 | 0.4 | 0.4 | 0.4 | 0.4 | 0.4 |
| ACRYJET 3666 (23.8 wt. % resin solids) | 2.1 | 6.3 | 2.1 | 6.3 | 2.1 | 2.1 | 2.1 |
| Polyethylene glycol (MW 400) | 7.5 | 7.5 | 7.5 | 7.5 | 7.5 | 7.5 | 7.5 |
| Dionized water | 75.8 | 71.6 | 75.8 | 71.6 | 75.8 | 75.8 | 75.8 |
| Total | 100 | 100 | 100 | 100 | 100 | 100 | 100 |
| P. Size | 110 | 123 | 161 | 173 | 126 | 200 | 180 |
| Optical density | 1.28 | 1.26 | 1.11 | 1.14 | 1.29 | 1.29 | 1.28 |

TABLE 1-continued

| Component | Sample 1 | Sample 2 | Sample 3 | Sample 4 | Sample 5 | Sample 6 | Sample 7 |
| --- | --- | --- | --- | --- | --- | --- | --- |
| Idle time (sec.) | 6 | 2 | 36 | 36 | 10 | >30 | >30 |
| Drying time (sec.) | 9.7 | 8.8 | 8.8 | 8.4 | — | — | — |

[1]Self-dispersing carbon black
[2]Esterified, self-dispersing carbon black made according to Example 1.
[3]Carbon black dispersed in an acrylic terpolymer made by polymerizing methacrylic acid, stearyl methacrylate, and dimethylsiloxane. according to U.S. Pat. No. 5,714,538 to Beach et al.

As shown by the comparisons in Table 1, ink formulations 3, 4, 6 and 7 containing modified self-dispersing carbon black according to the invention exhibited substantially longer idle times than ink formulations containing un-modified self-dispersing carbon black. Idle times using the ink formulations of the invention were generally in the 30 second and greater range, whereas idle times of 2 to 12 seconds were exhibited by samples 1, 2 and 5.

It is contemplated, and will be apparent to those skilled in the art from the foregoing specification that modifications and/or changes may be made in the embodiments of the invention. Accordingly it is expressly intended that the foregoing are only illustrative of the preferred embodiments and is not limiting thereto and that the true spirit and scope of the present invention be determined by reference to the appended claims.

What is claimed is:

1. An ink jet printer ink formulation comprising a humectant, an organic solvent, a chemically modified carbon black pigment, and from about 50 to about 85 percent by weight water, wherein the chemically modified carbon black pigment contains steric inducing groups on a surface of the carbon black which groups are derived from a steric inducing compound, the compound being substantially soluble in the humectant and the compound being reactive with an organic acid halide, whereby the ink jet printer ink formulation containing the chemically modified carbon black has an idle time of greater than about 15 seconds in an ink jet printhead.

2. The ink formulation of claim 1 wherein the humectant comprises 1,2-hexanediol.

3. The ink formulation of claim 2 wherein the humectant is present in an amount ranging from about 0.5 to about 1.5 percent by weight of the ink formulation.

4. The ink formulation of claim 1 wherein the chemically modified carbon black pigment comprises from about 1 to about 10 percent by weight of the ink formulation.

5. The ink formulation of claim 1 further comprising a penetrant wherein the penetrant comprises diethylene glycol mono-n-hexyl ether (hexyl carbitol).

6. The ink formulation of claim 5 wherein the penetrant is present in the ink formulation in an amount ranging from about 0.2 to about 1.0 percent by weight of the ink formulation.

7. The ink formulation of claim 1 wherein the steric inducing compound is selected from the group consisting of monoalkoxy-terminated polyalkylene glycol compounds having an alkylene group containing from 2 to 6 carbon atoms and an alkyl group containing from 1 to 6 carbon atoms, alkoxy-terminated polyalkylene glycols having a number average molecular weight ranging from about 100 to about 1000 and alkoxy-terminated, mono-amine-terminated polyalkylene glycols having a weight average molecular weight ranging from about 500 to about 2500.

8. The ink formulation of claim 1 wherein the chemically modified carbon black pigment has an acid number ranging from about 0.1 to about 0.7.

9. An ink jet cartridge containing the ink formulation of claim 1.

10. A method for making an ink formulation for an ink jet printer comprising the steps of:
   reacting carbon black containing surface caboxyl groups thereon with thionyl halide under conditions sufficient to produce acid halide groups on the surface of the carbon black;
   reacting the carbon black containing acid halide groups on the surface thereof with a steric inducing compound to provide a chemically modified carbon black pigment containing steric inducing groups on the surface thereof;
   mixing from about 1 to about 10 percent by weight of a chemically modified carbon black pigment with a humectant, an organic solvent and from about 50 to about 85 percent by weight water to provide an ink formulation having improved idle time, wherein the steric inducing groups on the carbon black surface are derived from a steric inducing compound which compound is substantially soluble in the humectant and which compound is reactive with an organic acid halide, and wherein the chemically modified carbon black pigment has an acid number ranging from about 0.1 to about 0.7.

11. The method of claim 10 wherein the steric inducing compound is selected from the group consisting of monoalkoxy-terminated polyalkylene glycol compounds having an alkylene group containing from 2 to 6 carbon atoms and an alkyl group containing from 1 to 6 carbon atoms, alkoxy-terminated polyalkylene glycols having a number average molecular weight ranging from about 100 to about 1000 and alkoxy-terminated, mono-amine-terminated polyalkylene glycols having a weight average molecular weight ranging from about 500 to about 2500.

12. The method of claim 10 wherein the ink formulation contains a penetrant wherein the penetrant comprises diethylene glycol mono-n-hexyl ether (hexyl carbitol).

13. The method of claim 12 wherein the penetrant is present in the ink formulation in an amount ranging from about 0.2 to about 1.0 percent by weight of the ink formulation.

14. The method of claim 10 wherein the humectant is present in an amount ranging from about 0.5 to about 1.5 percent by weight of the ink formulation.

15. The method of claim 14 wherein the humectant comprises 1,2-hexanediol.

16. An ink cartridge containing an ink formulation made by the method of claim 10.

* * * * *